US008044294B2

(12) United States Patent
Park et al.

(10) Patent No.: US 8,044,294 B2
(45) Date of Patent: Oct. 25, 2011

(54) THERMOELECTRIC MATERIALS AND DEVICES

(75) Inventors: Yeonjoon Park, Yorktown, VA (US);
Sang H. Choi, Poquoson, VA (US);
Glen C. King, Yorktown, VA (US);
James R. Elliott, Yorktown, VA (US);
Noel A. Talcott, Poquoson, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 356 days.

(21) Appl. No.: 12/254,016

(22) Filed: Oct. 20, 2008

(65) Prior Publication Data

US 2009/0165837 A1    Jul. 2, 2009

Related U.S. Application Data

(60) Provisional application No. 60/980,878, filed on Oct. 18, 2007, provisional application No. 60/980,881, filed on Oct. 18, 2007, provisional application No. 60/980,880, filed on Oct. 18, 2007, provisional application No. 60/980,871, filed on Oct. 18, 2007, provisional application No. 60/980,876, filed on Oct. 18, 2007, provisional application No. 60/980,870, filed on Oct. 18, 2007.

(51) Int. Cl.
*H01L 35/14* (2006.01)
*H01L 35/22* (2006.01)

(52) U.S. Cl. ........ 136/239; 136/200; 136/205; 136/203; 136/236.1; 438/54; 438/48

(58) Field of Classification Search .................. 136/202, 136/201, 205–212; 438/54; 257/1–39
See application file for complete search history.

(56) References Cited

U.S. PATENT DOCUMENTS

| 5,709,745 | A | 1/1998 | Larkin et al. |
|---|---|---|---|
| 6,306,211 | B1 | 10/2001 | Takahashi et al. |
| 6,562,127 | B1 | 5/2003 | Kud et al. |
| 6,627,809 | B1 * | 9/2003 | Koga et al. .................. 136/236.1 |
| 2007/0222034 | A1 * | 9/2007 | Park et al. ..................... 257/616 |
| 2008/0113186 | A1 * | 5/2008 | Kouvetakis et al. .......... 428/336 |
| 2008/0257395 | A1 * | 10/2008 | Jovanovic et al. ............. 136/239 |

OTHER PUBLICATIONS

Wado et al., Epitaxal Growth of SiGe on Al2O3 using Si2H6 Gas and Ge Solic Source Molecular Beam Epitaxy, Journal of Crystal Growth, vol. 169, pp. 457-462, 1996.*

* cited by examiner

*Primary Examiner* — Jennifer K. Michener
*Assistant Examiner* — Jayne Mershon
(74) *Attorney, Agent, or Firm* — Thomas K. McBride, Jr.; Linda B. Blackburn

(57) ABSTRACT

New thermoelectric materials comprise highly [111]-oriented twinned group IV alloys on the basal plane of trigonal substrates, which exhibit a high thermoelectric figure of merit and good material performance, and devices made with these materials.

24 Claims, 13 Drawing Sheets

Single Crystal SiGeCSn

Highly Oriented Twinned SiGeCSn

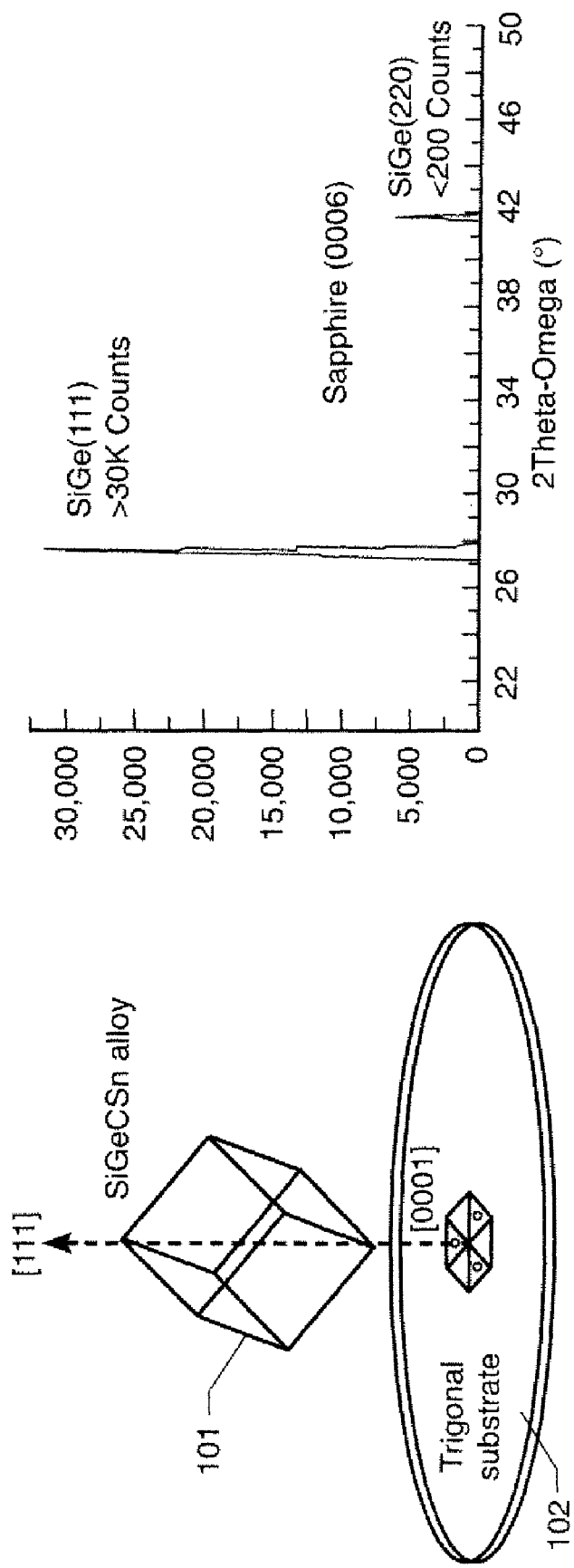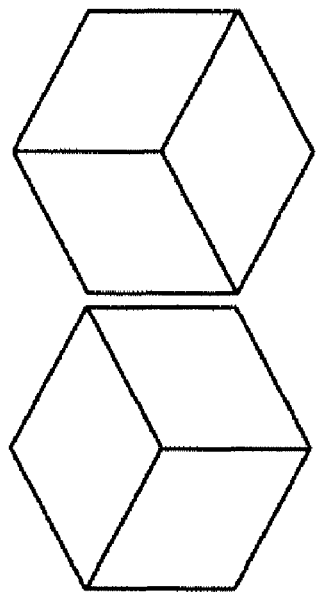
Fig. 01a
Fig. 01b
Fig. 01c

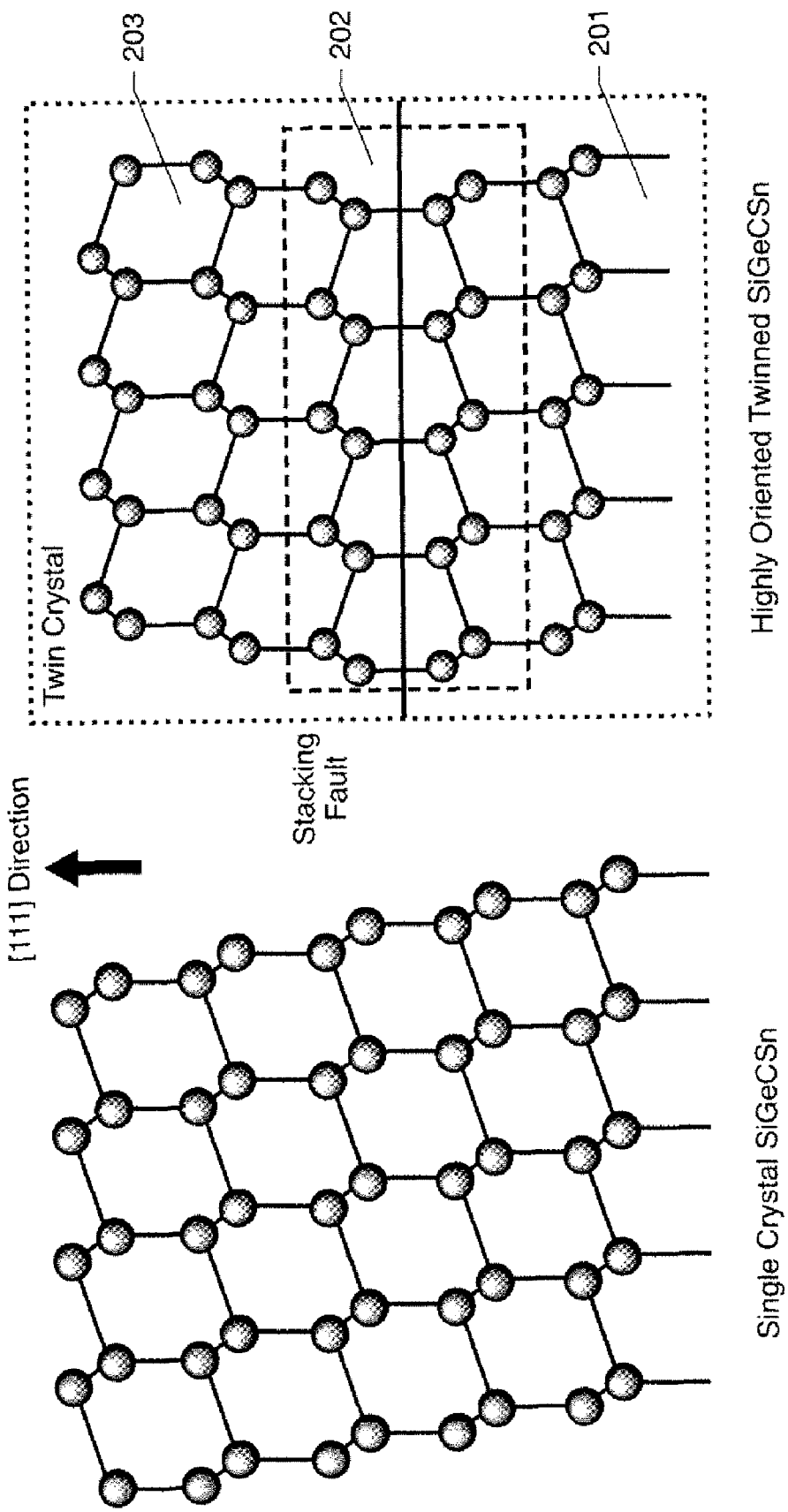
Fig. 02b — Highly Oriented Twinned SiGeCSn
Fig. 02a — Single Crystal SiGeCSn

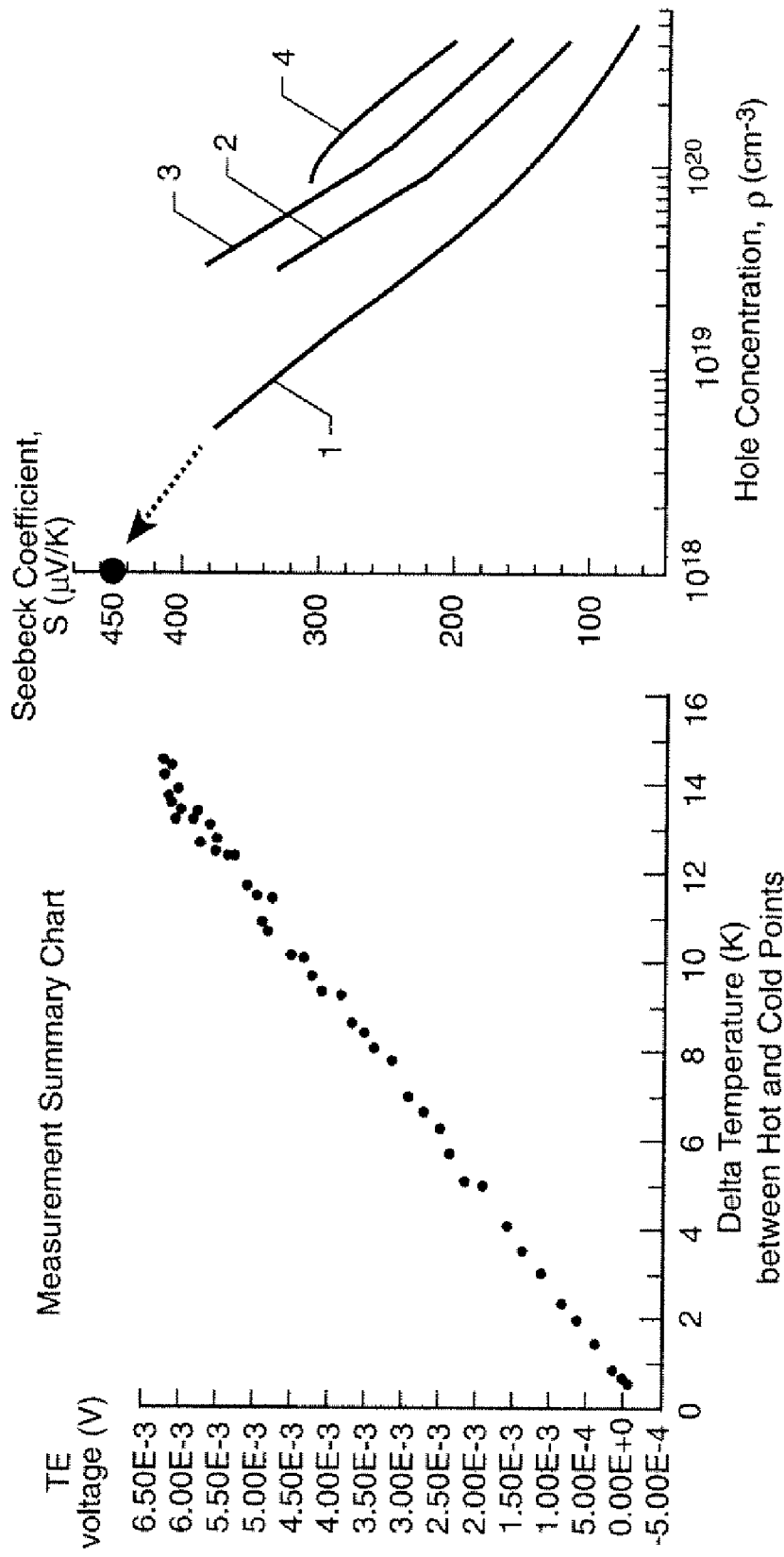

Fig. 06

(Left) Thermoelectric Voltage (V) vs. Delta Temperature (K). (Right) Seebeck coefficient vs. p-type doping concentration in single crystalline $Si_{1-x}Ge_x$. Round mark: measured Seebeck coefficient of highly oriented twinned SiGe sample at 300K, solid lines are for general SiGe alloy at different temperatures after Dismukes et al., Journal of Physical Chemistry 68, 3021 (1964), 1: T = 300K (x = 0.2, 0.3, 0.4), 2: T = 600K (x = 0.3), 3: T = 900K (x = 0.3), 4: T = 1200K (x = 0.3).

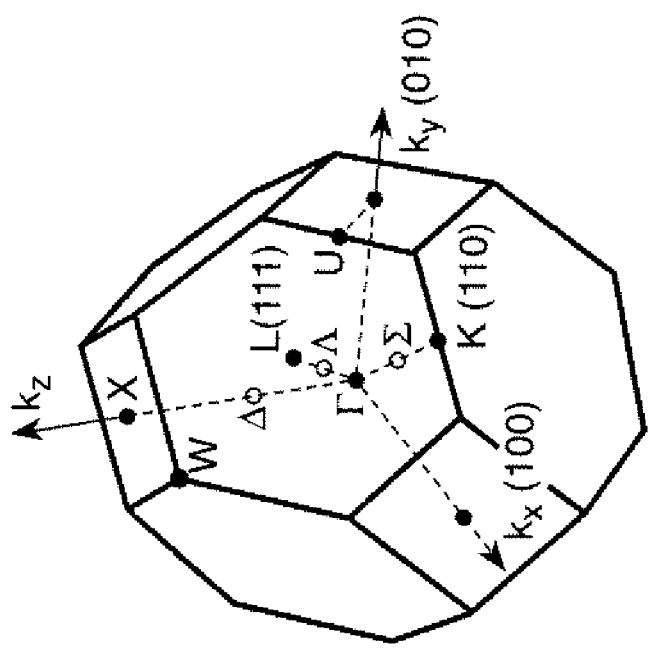
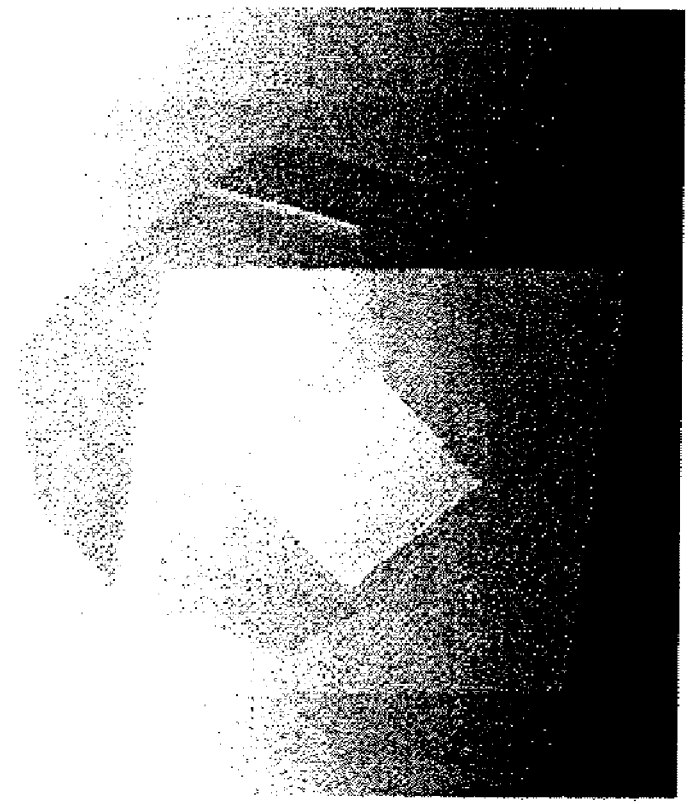
Fig. 07

Known Art

Scattered phonon in highly oriented twinned SiGeCSn

Propagating phonons in single crystalline SiGeCSn

Phonon at L-point

Phonons at three X-points

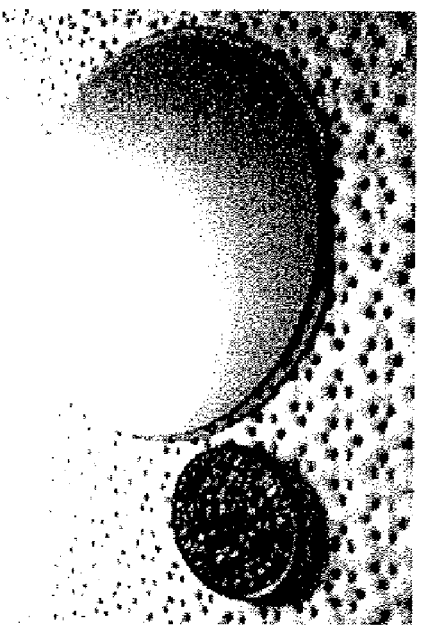
Fig. 11a
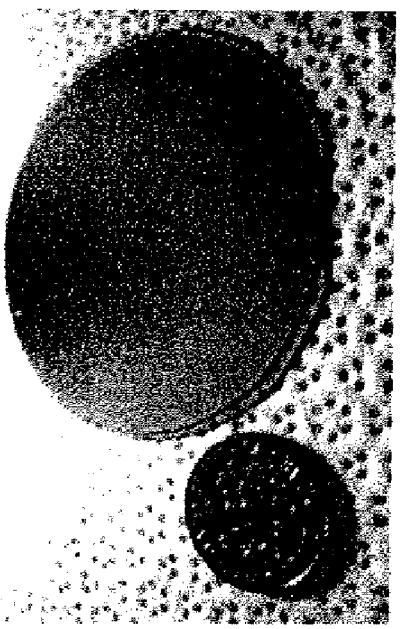
Fig. 11b

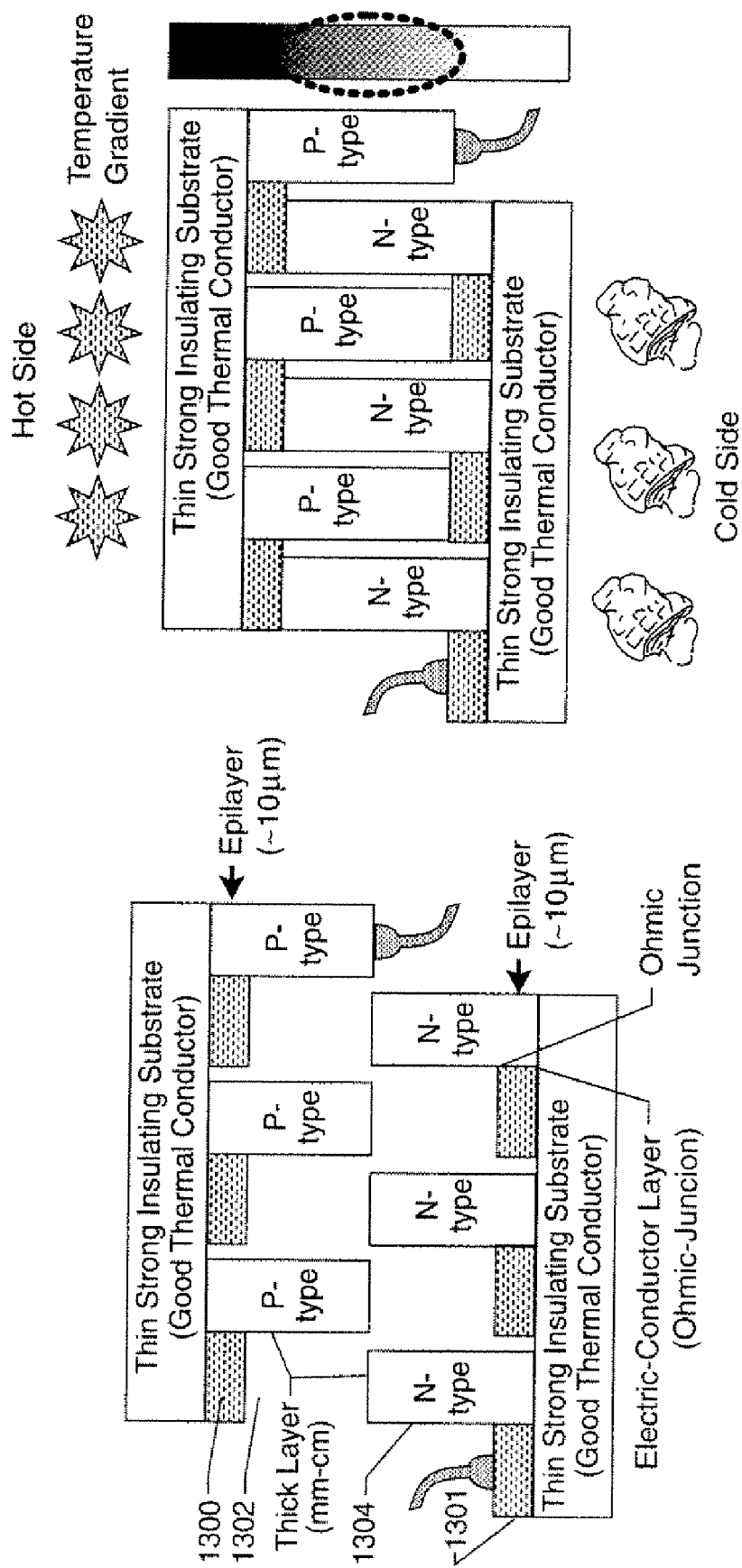

THERMOELECTRIC MATERIALS AND DEVICES

ORIGIN OF THE INVENTION

This invention was made in part by employees of the United States Government and may be manufactured and used by or for the Government of the United States of America for governmental purposes without the payment of any royalties thereon or therefor.

CROSS-REFERENCE TO RELATED APPLICATIONS

This application claims the benefit of the respective filing dates of, and incorporates by reference the entire respective disclosures of, the following commonly assigned U.S. Provisional Patent Applications: Ser. No. 60/980,870 filed on Oct. 18, 2007, Ser. No. 60/980,871 filed on Oct. 18, 2007, Ser. No. 60/980,876 filed on Oct. 18, 2007, Ser. No. 60/980,878 filed on Oct. 18, 2007, Ser. No. 60/980,880 filed on Oct. 18, 2007, and Ser. No. 60/980,881 filed on Oct. 18, 2007, each of which contains an overlap of inventive entity with the present application. In addition, this application incorporates by reference the entire disclosures of the following commonly assigned nonprovisional U.S. patent applications being filed on the same date as the present application: Ser. No. 12/254,017, entitled "EPITAXIAL GROWTH OF CUBIC CRYSTALLINE SEMICONDUCTOR ALLOYS ON BASAL PLANE OF TRIGONAL OR HEXAGONAL CRYSTAL;" Ser. No. 12/254,134, entitled "HYBRID BANDGAP ENGINEERING FOR SUPER-HETERO-EPITAXIAL SEMICONDUCTOR MATERIALS, AND PRODUCTS THEREOF;" Ser. No. 12/288,379, entitled "RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS;" Ser. No. 12/288,380, entitled "X-RAY DIFFRACTION WAFER MAPPING METHOD FOR RHOMBOHEDRAL SUPER-HETERO-EPITAXY;" and Ser. No. 12/254,150, entitled "METHOD OF GENERATING X-RAY DIFFRACTION DATA FOR INTEGRAL DETECTION OF TWIN DEFECTS IN SUPER-HETERO-EPITAXIAL MATERIALS;" each one claiming priority to the above-cited provisional applications.

BACKGROUND OF THE INVENTION

1. Field of the Invention

The present invention is in the field of semiconductor materials, and more particularly thermoelectric materials and devices made with highly [111]-oriented twinned group IV semiconductor alloys on the base plane of trigonal substrates.

2. Description of the Related Art

Solid-state thermoelectric devices convert temperature differences into electricity, or develop a temperature difference when a voltage is applied. Thermoelectric effects in semiconductor junction devices include (among others) the Seebeck Effect. The Seebeck Effect is due to a combination of charge carrier diffusion and phonon drag.

Charge carrier diffusion, in semiconductors made from n- and p-doped materials, results when electrons and holes diffuse in response to a temperature gradient. The diffusing charges are scattered by impurities, imperfections and lattice vibrations (phonons). Since the scattering is energy dependent, a charge density differential will develop in response to a temperature gradient. The magnitude of the effect tends to increase with the electrical conductivity of the material, and to decrease with its thermal conductivity. However, there are interdependencies of these characteristics, which have added to the difficulty of developing good thermoelectric materials.

While good semiconductor device materials require a single crystalline phase without defects, many good thermoelectric materials have electrically connected poly-type crystalline structures that scatter phonons, thus reducing thermal conductivity. For example, thermoelectric skutterudite material has three pnictogen square planes that can orient randomly. See M. Formari, D. J. Singh, I. I. Mazin, and J. L. Feldman, in MRS Symposium Proceedings 626, Thermoelectric Materials 2000—The Next Generation Materials for Small-Scale Refrigeration and Power Generation Application, 2000, p. Z6.3.1. One material that has particularly been employed for thermoelectric purposes is Skutterudite CoSb, which has many poly-type structures to scatter phonons, yet the structures are electrically connected.

As another example, U.S. Pat. No. 6,207,886 teaches the use of a Co—Sb-based filled-skutterudite sintered material having a lower thermal conductivity and thereby having a higher figure of merit. This reference teaches a formulation involving fine crystals, in which the areas at the boundaries of the fine crystal grains are increased, phonon scattering is enhanced, the thermal conductivity is decreased, and the figure of merit is increased.

Thermoelectric devices have been made from other materials, such as silicon-germanium (SiGe), but these have conventionally exhibited lower figures of merit. While Skutterudite CoSb has a good figure of merit, it can perform only at intermediate operating temperatures. Because electric output is proportional to operating temperature, SiGe thermoelectric materials have been preferred for many applications because of their ability to operate at higher temperatures. Similar performance has been seen with other group IV variants, including various alloys of silicon, germanium, carbon and/or tin. However, previously known SiGe and other group IV thermoelectric materials have a relatively low figure of merit due to their high thermal conductivity.

SUMMARY OF THE INVENTION

It is an object of the invention to provide SiGe and/or other group IV thermoelectric materials, formulated in compositions that exhibit improved thermoelectric properties, but can operate at the higher temperatures previously provided by SiGe and group IV devices.

It is a further object of the invention to provide thermoelectric and other devices made of such materials, to take advantage of the high-temperature and high figure of merit characteristics of those materials.

In response to these objectives, the present invention provides new noble thermoelectric materials and devices comprising highly [111]-oriented twinned group IV alloys on the basal plane of trigonal substrates, which exhibit a high thermoelectric figure of merit and good material performance, as well as devices made with these materials.

To achieve these results, the present invention generally involves, in one embodiment, materials comprising alloys of two or more of carbon (C), silicon (Si), germanium (Ge), and tin (Sn) (referred to, in any relative composition, as "SiGeCSn") grown as highly [111]-oriented twinned crystal structures on the basal plane of a trigonal substrate (such as, by way of example, sapphire). Such crystal structures can reduce thermal conductivity by scattering lattice vibration while keeping good electrical conductivity and Seebeck coefficient.

Exemplary thermoelectric devices may be made with highly [111]-oriented twinned SiGeCSn on the basal plane of trigonal substrate with n-type and p-type doping, in which one such wafer with n-type doping is vertically bonded with another such wafer with p-type doping, and either a series or parallel electrical circuit is made on the wafer, for example with heavily doped materials, metallic materials, or indium tin oxide, etc.

Other aspects and advantages of the invention will be apparent from the accompanying drawings, and the detailed description that follows.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which:

FIG. 1 shows (a) the crystal orientation of SiGeCSn alloy on the basal plane of trigonal substrate such as sapphire, (b) symmetric normal X-ray diffraction data of thick SiGe layer (>6 μm) on sapphire and (c) rhombohedral "twinning."

FIG. 2 shows the crystal structure of (a) single crystalline SiGeCSn alloy, and (b) highly oriented twinned SiGeCSn alloy with stacking faults and twin crystal.

FIG. 6 shows (Left) Thermoelectric Voltage (V) vs. Delta Temperature (K) and (Right) general trend lines of dependence of Seebeck coefficient on p-type doping concentration in single crystalline $Si1-xGe_x$ from Dismukes et al., Journal of Physical Chemistry 68, 3021 (1964); plot 1: T=300K (x=0.2, 0.3, 0.4), plot 2: T=600K (x=0.3), plot 3: T=900K (x=0.3), plot 4: T=1200K (x=0.3).

FIG. 7 shows (Left) First Brillouin Zone of diamond structure and (Right) orientation names and Miller indices in the First Brillouin Zone.

FIG. 11 shows pictures of fabricated (a) p-type and (b) n-type, highly oriented twinned SiGe thermoelectric materials on c-plane sapphire.

FIG. 13 shows (a) p-type and n-type SiGeCSn alloy grown on two different basal plane trigonal wafers such as c-plane sapphire, with electrical circuit on substrate made with conducting materials such as metals, ITO, etc., (b) assembled thermoelectric device made with two SiGeCSn/trigonal substrate wafers.

DETAILED DESCRIPTION

Figures 3A, 3B, 3C:
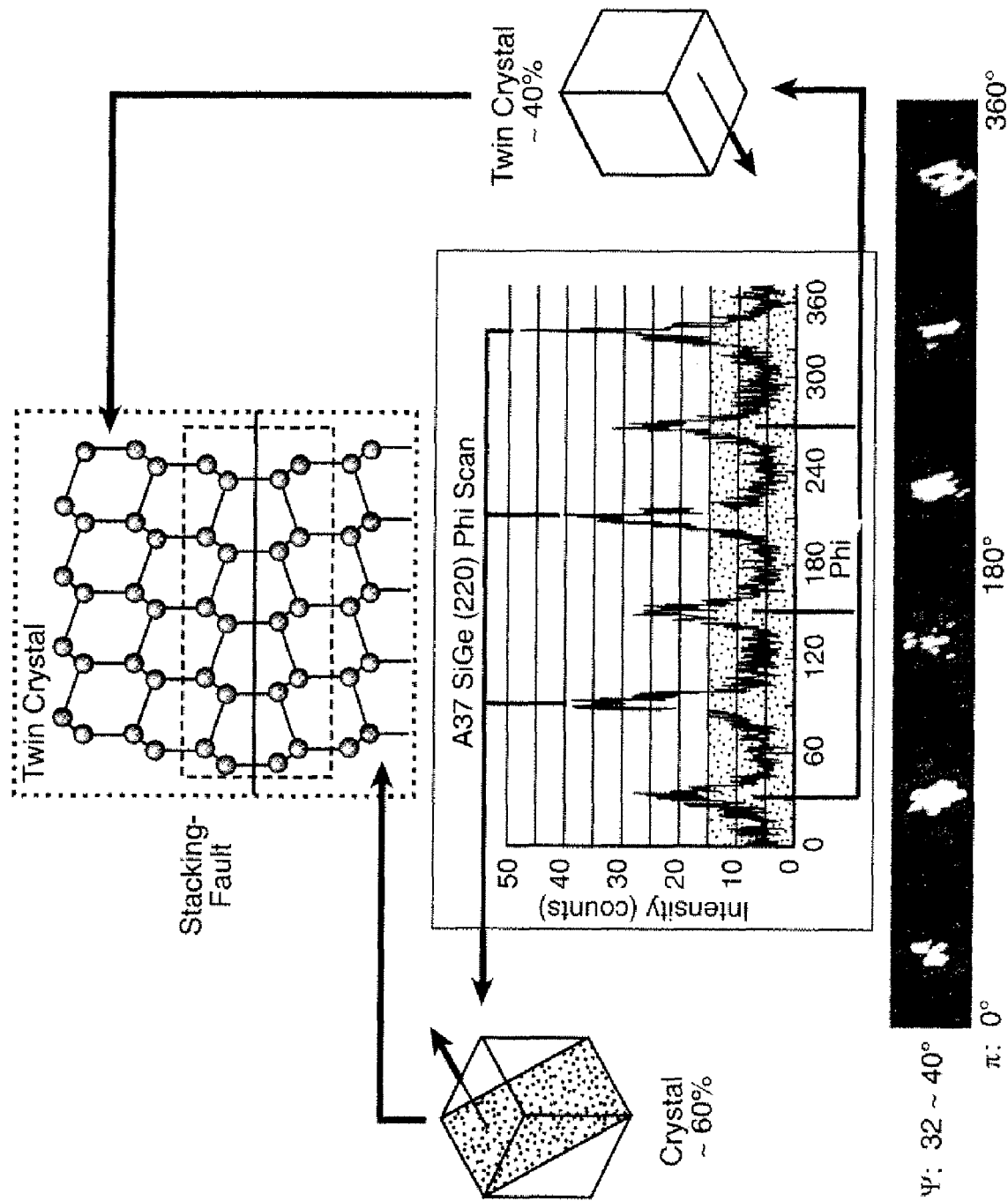
FIG. 3 shows XRD Data reflecting the concentration of twin crystals, where (a) upper block is a representation of the 60 degree rotated twin crystal, (b) XRD Data shows 60:40 ratio between majority SiGe crystal and minority twin SiGe crystal i.e. 60 degree rotated twin crystal, and (c) multi-axes (Phi vs. Psi) XRD scan confirms the unequal-ratio.

The following is a detailed description of certain embodiments of the invention chosen to provide illustrative examples of how it may preferably be implemented. The scope of the invention is not limited to the specific embodiments described, nor is it limited by any specific implementation, composition, embodiment or characterization depicted in the accompanying drawings or stated or described in the invention summary or the abstract. In addition, it should be noted that this disclosure describes a number of methods that each comprise a plurality of steps. Nothing contained in this written description should be understood to imply any necessary order of steps in such methods, other than as specified by express claim language.

In the ensuing description, the well-known Miller indices notation of lattice planes is used, That is, crystal planes are designated by numbers within "( )", groups of similar planes are designated by numbers within "{ }", direction or length is designated by numbers within "[ ]", and groups of similar directions are designated by numbers within "< >".

Cubic group IV crystals form on trigonal substrates (such as the basal plane of sapphire (Al2O3) in two azimuthal rhombohedral alignments. FIG. 1(a) shows rhombohedral alignment of a cubic crystal 101, wherein the <111> direction of the cubic crystal is aligned with the <0001> direction of the trigonal substrate 102. FIG. 1(c) shows two possible in-plane azimuthal alignments within a rhombohedral alignment. The two configurations are "twin" to each other. This atomic alignment allows poly-type crystalline structures with 60 degree-rotated twin defects as a result of stacking faults, as well as twinning on the interface with the underlying trigonal substrate. Another possibility is a 30 degree rotation between the projected lattice axis of the epitaxial layer and substrate later, referred to in disclosures that have been incorporated herein by reference as "Type A" and "Type "B" alignment.

FIG. 2 further illustrates the difference between single crystalline SiGeCSn alloy and highly-oriented twinned SiGeCSn alloy. The vertical direction of the picture is the [111] direction of the diamond structure. The block 202 between the two blocks 201 and 203 is the stacking fault, which rotates the crystal structure in the upper block 203 by 60°. Due to the trigonal symmetry of diamond structure along the [111] direction, a rotation with 60° and −60° is the same as rotation with 180°. Note that there is difference in the crystal structure between upper block 203 and lower block 201.

While other disclosures which have been identified above and incorporated herein by reference have focused on predominantly single-crystal structures, for example, lattice matched crystals, the embodiments of the present invention described below are focused on highly [111]-oriented SiGeCSn alloys with high density of stacking faults and twin crystals.

By "highly [111]-oriented" we mean that normal two-theta/theta scan of X-ray diffraction shows the (111) peak of SiGeCSn as stronger than any other (hkl) peaks of SiGeCSn, i.e. the majority of SiGeCSn material is aligned on the (trigonal) substrate as shown in FIG. 1(b), wherein more than 50% of atomic volume is aligned on trigonal substrate such that the

[111] direction of diamond structured alloy of any combination of Si, Ge, C, and Sn is parallel to the c-axis direction [0001] of the trigonal substrate as shown in FIG. 1(a). (In practice, as will be further discussed, more than 90% of [111] oriented SiGe material on c-plane sapphire as shown in FIG. 1(b) was achieved.)

By "twin crystals" or "twinned" (or "containing twin defects") we mean that, as shown in FIG. 3(b)—XRD Phi scan and FIG. 3(c)—Phi vs. Psi scan of the (220) peaks of SiGeCSn show six peaks, three of which belong to the original crystal and the other three belong to twin crystal. The peak height and area can be equal or not-equal to each other. (This XRD method is described in disclosures identified above which have been incorporated herein by reference. Also within the meaning of "twinned" as used in this disclosure is a mixture of crystals in rhombohedral orientations with and without a 30 degree rotation between the projected lattice axis of the epitaxial layer and substrate later, i.e., a mixture of "Type A" and "Type B" alignments.)

SiGeCSn alloy materials with a high density of stacking faults in {111} plane and 60 degree rotated twins are not necessarily harmful, but can in fact be beneficial to thermoelectric applications.

A good thermoelectric material requires high figure of merit (ZT factor), which is defined by $$ZT = S^2 \frac{\sigma}{\kappa} T$$

where
S=Seebeck coefficient (thermally generated open circuit voltage of material, micro-volts per Kelvin),
σ=Electrical conductivity (1/(W·cm)),
κ=Thermal conductivity (Watt/cm-K), and
T=Absolute temperature of operation (K).

It is evident from this equation that, in order to obtain a high ZT, it is desirable to achieve high σ (electrical conductivity), high S (Seebeck coefficient), and low κ (Thermal conductivity). Thermal conductivity is reduced in materials that internally scatter phonons (lattice vibrations).

The growth of SiGe (for example) on the trigonal (0001) plane of sapphire can scatter more phonons by utilizing the poly-type structures formed by twin crystals, thus increasing the thermoelectric figure of merit by reducing thermal conductivity. In short, the poly-type crystal structures made with stacking faults and twins can help the scattering of phonons while keeping electrical conductivity high, thus increasing the figure of merit (ZT) of thermoelectric SiGeCSn.

Material Fabrication

As explained in other disclosures incorporated herein by reference, rhombohedrally aligned, strained or lattice-matched layer(s) can be grown with various standard growth methods, including but not limited to, sputtering methods, Molecular Beam Epitaxy (MBE), Metal Organic Chemical Vapor Deposition (MOCVD), Metal Organic Chemical Vapor Phase Epitaxy (MOVPE), Hydride Vapor Phase Deposition (HVPE), Liquid Phase Epitaxy (LPE), Physical Vapor Deposition (PVD), and Pulsed Laser Deposition (PLD). To fabricate the final device structures, standard microfabrication technologies can be used, including but not limited to, lithography, etching, metallization, dopant diffusion/implantation and oxidation. The resulting cubic diamond semiconductor alloy on the trigonal substrate can be used "as is" or can be removed from the substrate after growth to a desired thickness. Such methods of removal are well known in the art and could include laser cutting, hydrogen cracking, etc., the choice of which is not a limitation of the present invention.

In the examples used for illustration, DC and RF-sputtering methods were used to grow a SiGe layer on c-plane sapphire. By changing the material growth condition such as growth temperature, flux ratio and/or sputtering power, we can control the density of stacking faults and twin crystals. Our XRD-related disclosures identified above and incorporated herein by reference report a new noble X-ray diffraction method to measure the ratio of twin crystal and underlying crystal. With SiGeCSn alloy on trigonal substrates, for example, sapphire, twin crystals can be formed by (1) double position defect at the interface between SiGeCSn and substrate and (2) stacking faults inside SiGeCSn layer.

In one series of examples, a 2-inch sapphire wafer was cleaned with acetone, iso-propanol, and deionized (DI)-water before transfer to a vacuum chamber. The sapphire wafer was baked at 200° C. to remove water vapors and then heated to 1,000° C. for a short time to remove any volatile contaminants. The temperature was monitored by thermocouple measurement near the wafer holder.

The growth temperature of all SiGe layers in this particular study was 820° C. The temperature was monitored by thermocouple measurement near the wafer holder. This temperature was chosen after numerous different growth runs in order to illustrate sensitive changes in the primary twin crystal concentration with respect to the growth parameters. (In other studies, documented in disclosures identified above which have been incorporated herein by reference, other temperatures, including 850° C. were used. The discussion in the present disclosure, and the results and conclusions expressed, primarily relate to observations at the 820° C. temperature.)

Seven (7) sccm (standard cubic centimeters per minute) of high purity Argon gas was used in the sputtering process. Three SiGe samples were grown at 820° C. with different DC sputtering powers of 150 watts, 200 watts, and 300 watts. An equal DC power was applied to Si and Ge target materials. The X-ray diffraction analysis of the SiGe (111) peaks shows that all the samples have the composition of $Si_{0.15}Ge_{0.85}$ due to the higher sputtering yield of Ge. By increasing DC power, the kinetic energies of Si and Ge species and the overall flux of Si and Ge increased.

While depositing Si and Ge with the DC sputtering method, boron was co-sputtered and mixed into the SiGe layer as p-type dopant using the RF-sputtering gun. The RF-sputtering power of boron was only about 1-3 watts, which resulted in the heavy doping of above $10^{19}/cm^3$.

After the growth was completed, the samples were analyzed with a 4-circle X-ray diffractometer and thermal diffusivity/Seebeck coefficient measurement system. Numerous other samples, comprising Si, Ge, C and Sn, were prepared by similar methods, varying the compositions and growth parameters such as temperature, sputtering power, chamber pressure, as well as doping, and these samples were analyzed comparably.

XRD Observations and Discussion

The analysis of many SiGe samples indicates the initial ratio of majority crystal and minority twin crystal is not 50:50 but close to 60:40 on c-plane sapphire in certain epitaxial growth condition. The data is shown in FIG. 3, with relation to stacking faults. The relationship to double position defect is not shown in this figure.

The unequal ratio means that there exists a difference in the formation energy when SiGe crystal layer is grown on top of trigonal sapphire substrate, We found that the SiGe crystal whose [220] direction is 60 degree rotated from sapphire's [1-104] direction is energetically favored, such that it can have 60 percent concentration. On the other hand, SiGe crystal whose [220] direction is parallel to sapphire's [1-104] direction has energetic disadvantage, such that it can have 40 percent concentration. Therefore the double position defect at the SiGe and sapphire interface can generate a not-equal ratio.

Nevertheless, many SiGe layers with high density of stacking faults have a 50:50 ratio of twin crystal. The XRD method reported in the above-identified disclosures incorporated herein by reference can be used to estimate the density of stacking faults, i.e. degree of twin crystal disorder, such that a non-equal ratio, such as 60:40 as the twin crystal made by double position defect at the SiGe-sapphire interface and 50:50 as the full disorder—high density of twin crystals made by stacking faults.

Figures 4A, 4B:
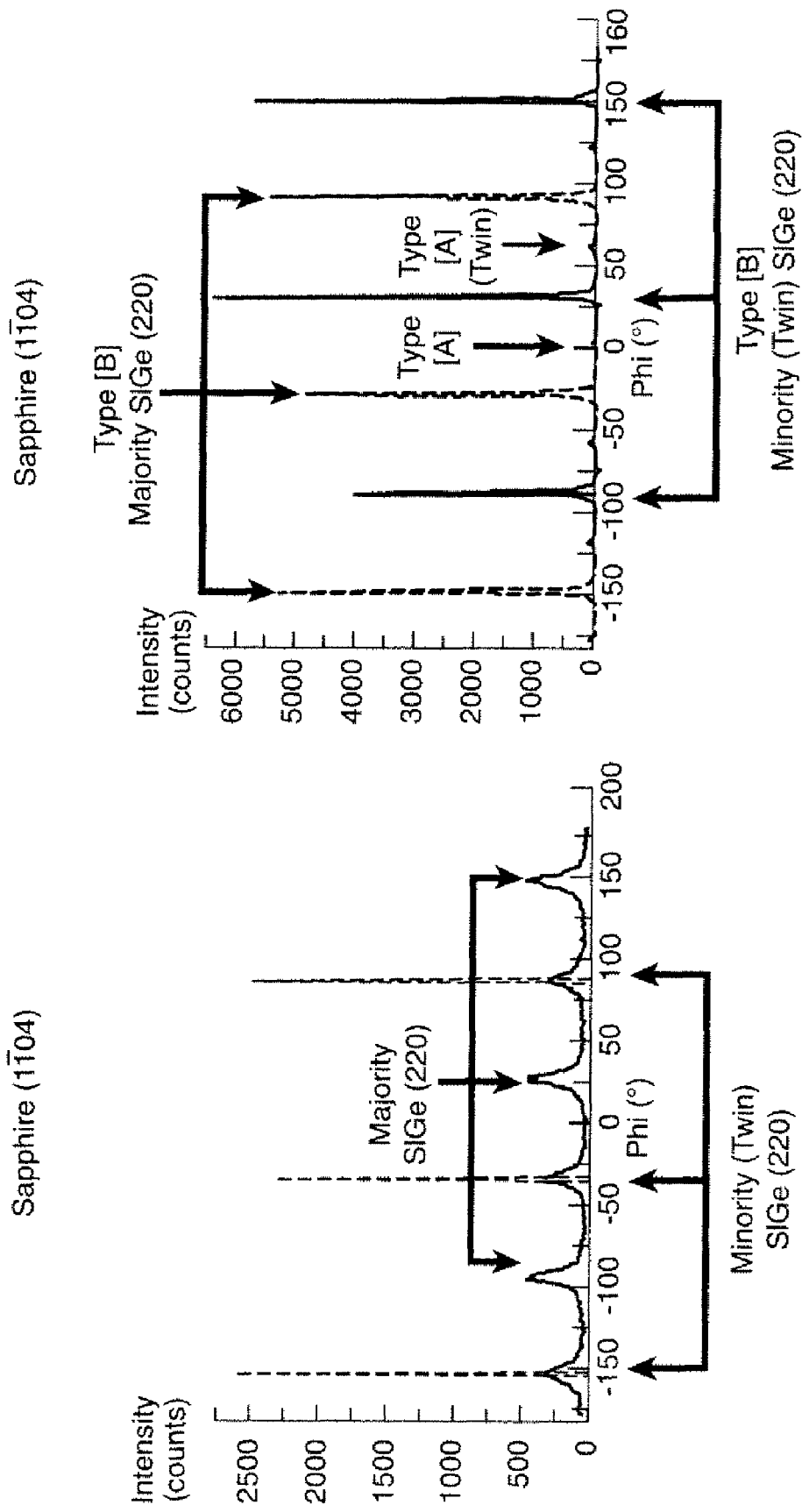
FIG. 4 shows Phi scan of SiGe(220) and sapphire (1-104) peaks, (a) Sample #A37—whole SiGe in type B alignment and (b) Sample #A313—mixture of type B and type A alignment.

It is important to note that the general trend is that the majority crystal's (220) peak is located at a 60 degree rotated position between sapphire (1-104) peaks as shown in FIG. 4. We observed some randomly mixed samples with 50:50 ratio but we did not observe any sample that was opposite to the general trend.

The foregoing describes the material structure of our SiGe layer on c-plane sapphire substrate. This entire discussion is generally applicable to any SiGeCSn alloy on any c-plane trigonal substrate.

Figure 5:
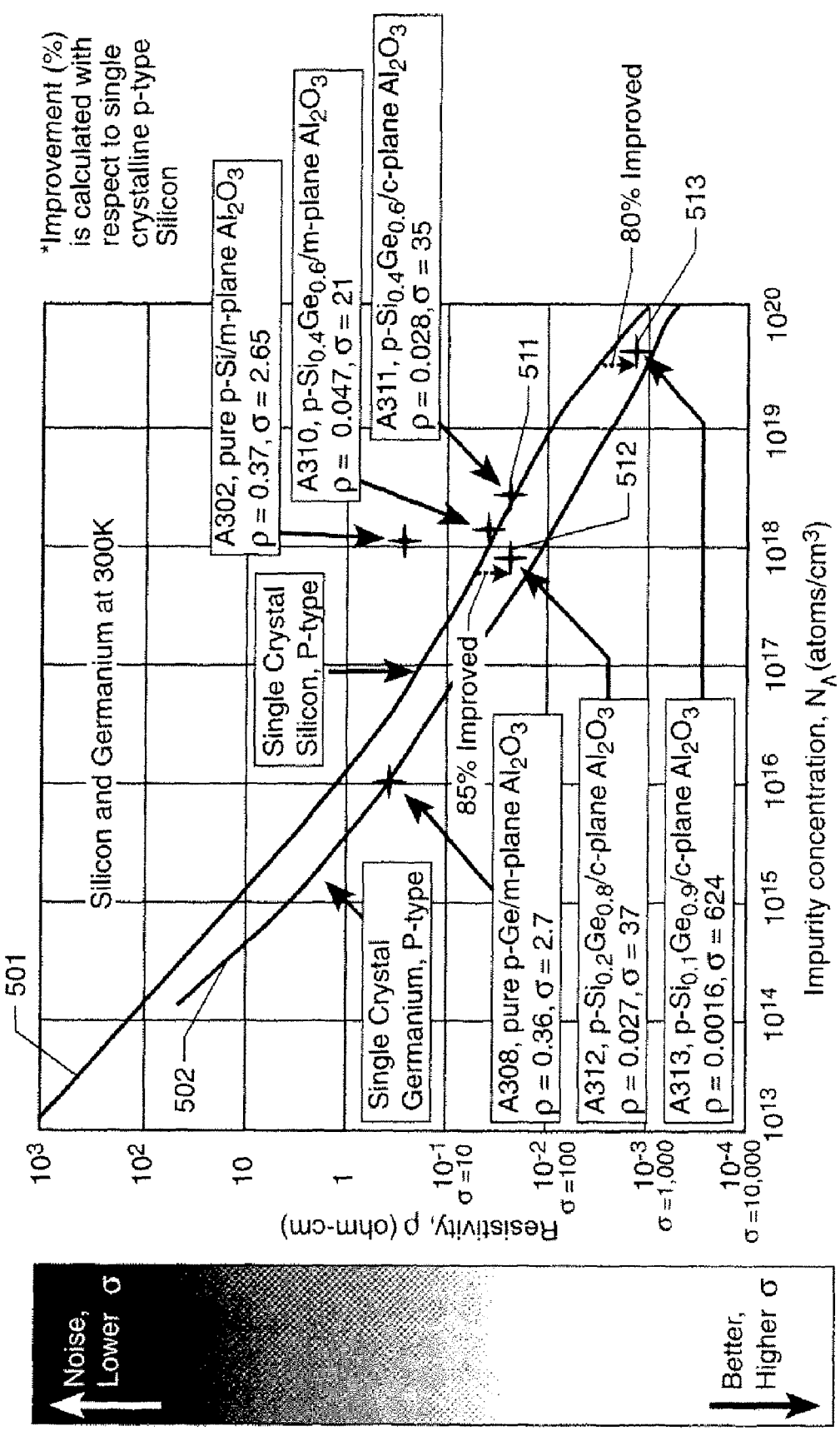
FIG. 5 is a graph showing resistivity vs. doping concentration for single crystalline Si and Ge with measured data-point (cross marks) of highly oriented twinned SiGe on sapphire.

As previously discussed, in order to obtain a high figure of merit (ZT), it is desirable to achieve high σ (Electric conductivity), high S (Seebeck coefficient), and low κ (Thermal conductivity). We measured the electric conductivity and doping concentration of p-type highly oriented twinned SiGe on sapphire with a Hall Effect measurement system. The measured data is shown in FIG. 5. The data plotted includes observations for the following samples: Sample A302 (pure p-Si/m-Al2O3, p=0.37, σ=2.65, Ge:0); Sample A308 (pure p-Ge/m-Al2O3, p=0.36, σ=2.7, Ge:1); Sample A310 (p-SiGe/m-Al2O3, p=0.047, σ=21, Ge:0.6); Sample A311 (p-SiGe/c-Al2O3, p=0.028, σ=35, Ge:0.6); Sample A312 (p-SiGe/c-Al2O3, p=0.027, σ=37, Ge:0.8); Sample A313 (p-SiGe/c-Al2O3, p=0.0016, σ=624, Ge:0.9).

In this chart, the lower is the better with higher a (electrical conductivity). Line 501 is for single crystalline p-type Si and line 502 is for single crystalline p-type Ge. These solid lines were included as comparison from multiple references. See R. C. Jaeger, Introduction to microelectronic fabrication, Vol. V, 2nd. ed. (Prentice Hall, 2002); D. B. Curtis, Bell Syst. Techn. 40, 509-523 (1961).

From FIG. 5, it appears that many SiGe materials on c-plane sapphire have higher σ (electrical conductivity) than SiGe on m-plane sapphire. Sample #A313 was slightly contaminated with Cu on the surface because Ge target material was depleted and underlying Cu electrode was sputtered. Substitutional Cu in Si and Ge acts as triple acceptor, p-type dopant while interstitial Cu in Si and Ge is single donor, i.e. n-type dopant. Since the ratio of substitutional Cu in Ge to interstitial Cu in Ge is 6:1 at room temperature (R. N. Hall and J. H. Racette, Journal of Applied Physics 35, 379-& (1964)), Cu acts as p-type dopant in #A313-$Si_{0.1}Ge_{0.9}$. Hall Effect measurement also showed that A313 is strong p-type material.

X-ray diffraction analysis showed that all samples with SiGe layers on c-plane sapphire belong to the highly oriented twinned SiGeCSn alloy crystals. The data points with cross-marks (511, 512, 513), are for A311, A312 and A313, which are between single crystalline p-type Si (501) and single crystalline p-type Ge (502). Therefore, this data indicates that the electrical conductivity of highly-oriented twinned SiGe on c-plane sapphire can be comparable to single crystalline SiGe. We conclude that the 60 degree rotated twinning with stacking faults does not drop the electrical conductivity severely, and the material—highly-oriented twinned SiGeCSn on basal plane of trigonal substrate (sapphire in this case) can keep moderately high electrical conductivity, σ.

The left-hand chart in FIG. 6 shows the measured thermoelectric voltage (at 300K) from one of the p-type highly-oriented twinned SiGe on c-plane sapphire samples. X-axis is the temperature difference in Kelvin and Y-axis is the generated thermoelectric voltage in Volts. Positive slope means that it is p-type material and the measured averaged Seebeck coefficient is about 450 μV/K at the doping concentration around $10^{18}/cm^3$. Therefore, this data indicates that our thermoelectric material is comparable to single crystalline SiGe thermoelectric material, as shown in the right chart in FIG. 6 for comparison. (Seebeck coefficient vs. p-type doping concentration of highly oriented twinned SiGe sample[round mark] and generic single crystalline $Si(1-x)Ge_x$[solid lines], plot 1: T=300K (x=0.2, 0.3, 0.4), plot 2: T=600K (x=0.3), plot 3: T=900K (x=0.3), plot 4: T=1200K (x=0.3) (solid lines are after J. P. Dismukes, R. S. Paff, and L. Ekstrom, Journal of Physical Chemistry 68, 3021 (1964)).

In order to understand the twinning effect on thermal properties, we have to consider the phonon dispersion in the reciprocal lattice of a diamond structure. The unit cell of the reciprocal lattice is the First Brillouin Zone as shown in FIG. 7. The name of each crystal orientation is given with Miller indices. Note that [111] direction is called the L-point, the [100] direction is called the X-point, and [110] direction is called the K-point. Similarly, halfway to the L-point is the Λ-point, halfway to the X-point is the Δ-point, and halfway to the K-point is the Σ-point. See N. W. Ashcroft and N. D. Mermin, Solid State Physics (Harcourt College Publishers, 1976).

Figure 8:
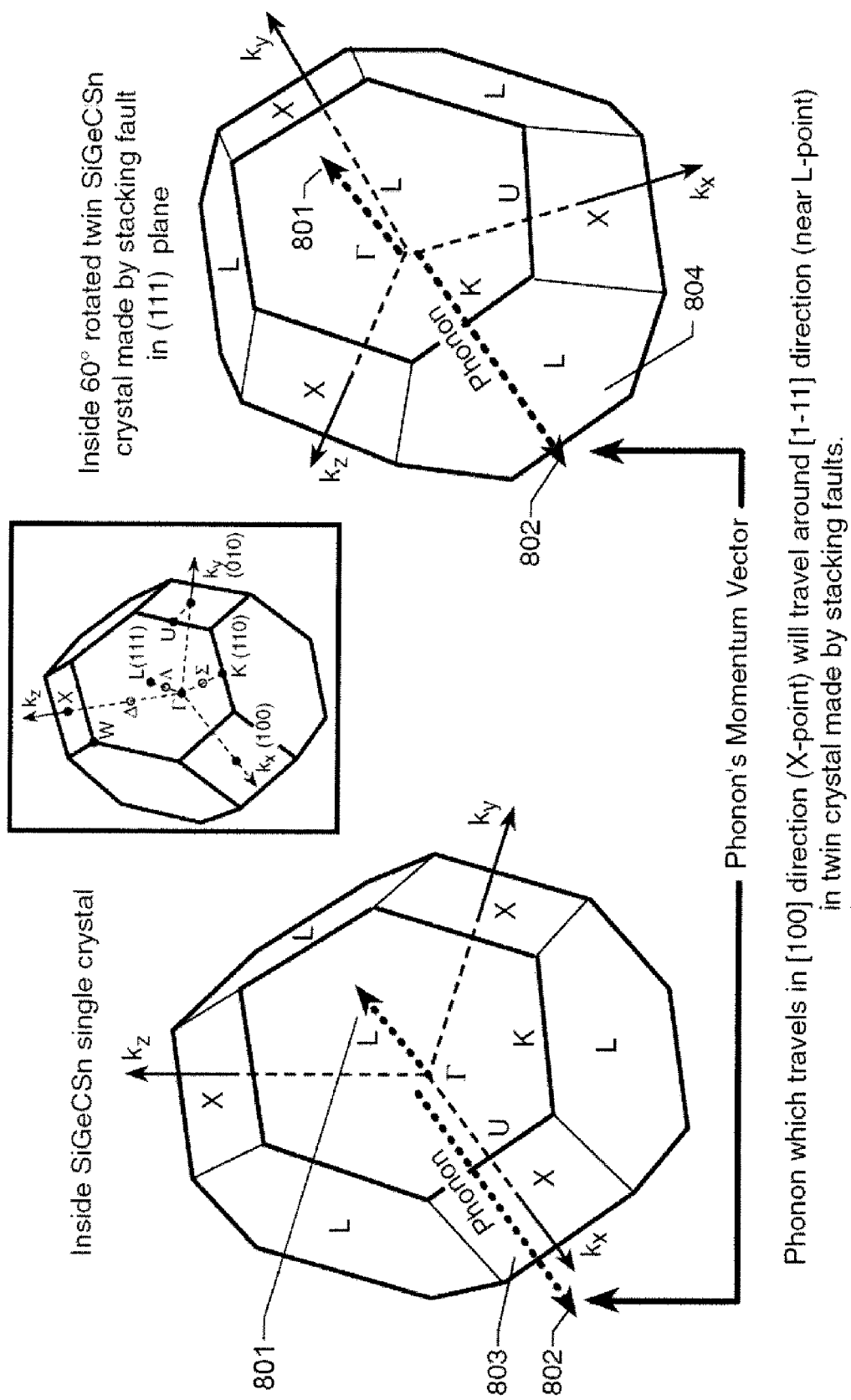
FIG. 8 shows relative orientation of First Brillouin Zones in (Left) diamond crystal and (Right) twin crystal made by stacking faults.

The effect of a twin crystal made by stacking faults is as follows. The twin crystal in the upper block 203 in FIG. 2(b) is rotated by 60 degrees in the {111} plane from the underlying crystal substrate. Therefore, the First Brillouin Zone inside the twin crystal is rotated by 60 degrees in the {111} plane as shown in FIG. 8.

The traveling phonon in the [111] direction, i.e. L-point, is drawn in dotted vector 801. The length of this vector is the momentum of the phonon. In the twin crystal's First Brillouin zone, the phonon travels the same direction (L-point) as the original crystal.

On the other hand, the traveling phonon (dotted vector 802) in X-point 803 ([100] direction) in the original crystal will be headed into a new orientation, the L-point 804 ([101] direction) in the twin crystal made by stacking faults. Note that the direction and length of momentum vector (dotted arrow 802) is the same in both First Brillouin Zones. In summary, we found that the traveling phonons in the X-point of the original crystal will face a new direction, L-point in the twin crystal.

Figure 9:
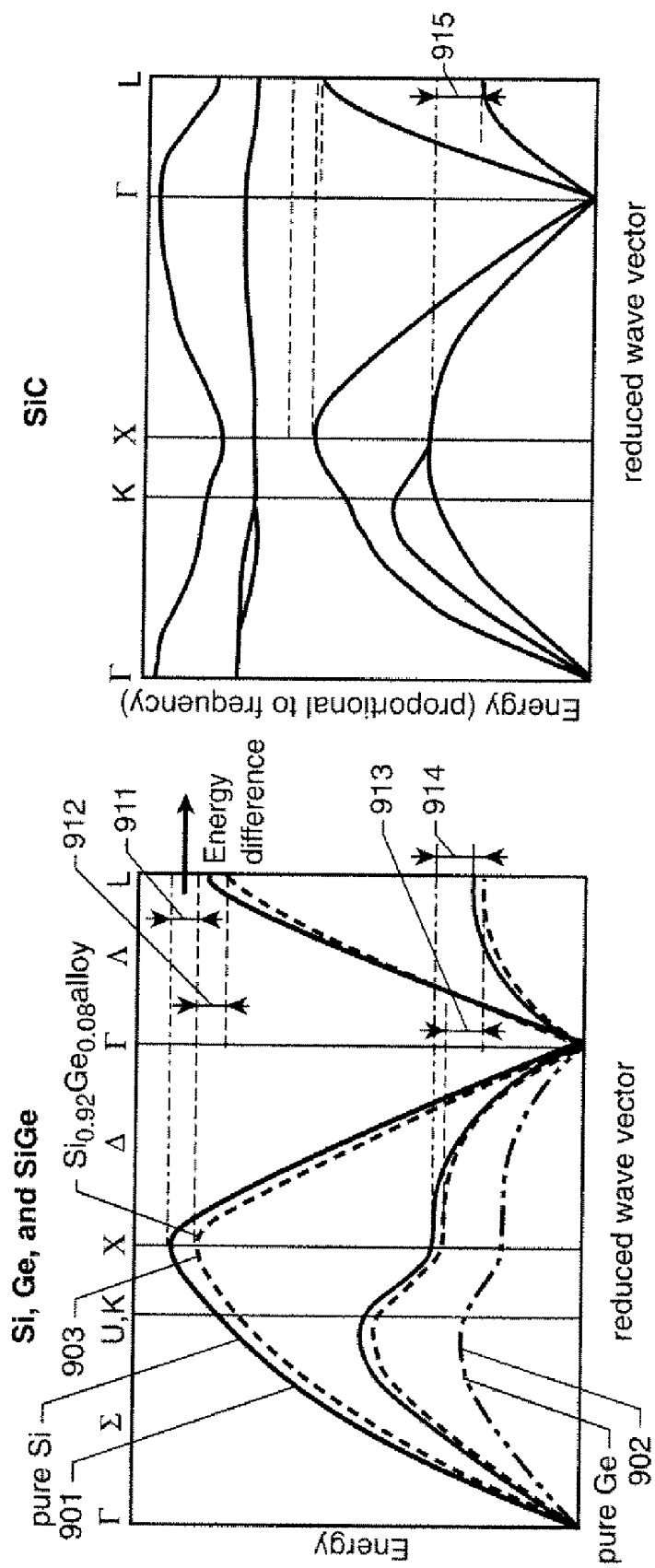
FIG. 9 shows energy differences between X point and L point of (Left) SiGe and (Right) SiC alloy. General trend lines of phonon dispersion curves of (a) SiGe and (b) SiC based on D. Le Bolloc'h et al., Phys. Rev. B, 63, 035204 and from J. Serrano et al., Appl. Phys. Lett. 80 (23) 4360.

Phonon dispersion curves of SiGe are shown in FIG. 9. FIG. 9 shows scattering of phonons at the stacking faults between twin crystal and underlying original crystal. The left panel (D. Le Bolloc'h, J. L. Robertson, H. Reichert, S. C. Moss, and M. L. Crow, Physical Review B 63, art. no. 035204 (2001)) shows acoustic phonon dispersion of the $Si_{0.92}Ge_{0.08}$ alloy in the (110) plane. The dispersion of pure Si is given by the solid line 901 and that of pure Ge by the dotted line 902. Dashed line 903 shows the total dispersion of the alloy. The right panel (J. Serrano, et al., Appl. Phys. Lett. 80 (23) 4360) shows phonon dispersion relations of 3C—SiC. The x axes are scaled in reciprocal lattice units.

Note that there exists a difference of the phonon bands between Γ-X direction and Γ-L direction. Therefore when a phonon near the X-point in the original crystal enters the twin crystal, it will go into L-point phonon bands of the twin crystal by the conservation of momentum. However, the phonon band in L-point in the twin crystal has a different energy from the X-point phonon band in the original crystal. (See arrows 911, 912, 913, 914, 915.) Therefore, the phonon in twin crystal cannot propagate as it did in the original crystal.

Figure 10B:
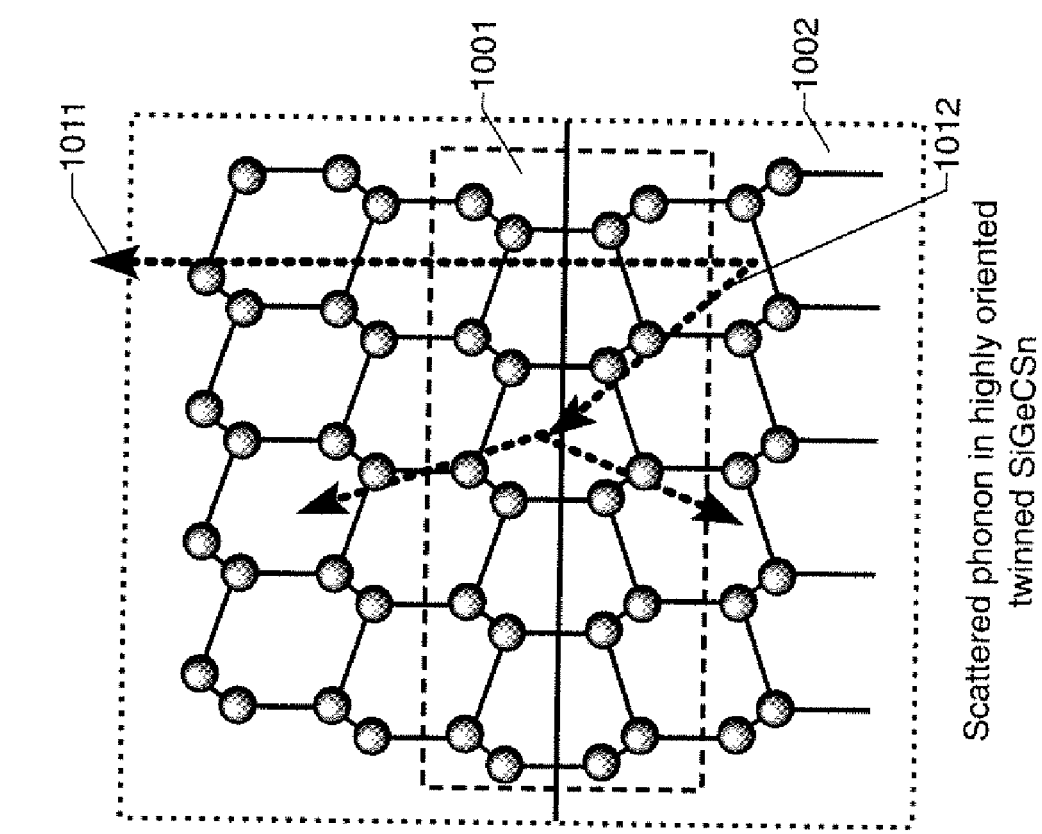
FIG. 10 shows scattering of phonons at the stacking faults between (a) underlying original crystal and (b) twin crystal.
Figure 10A:
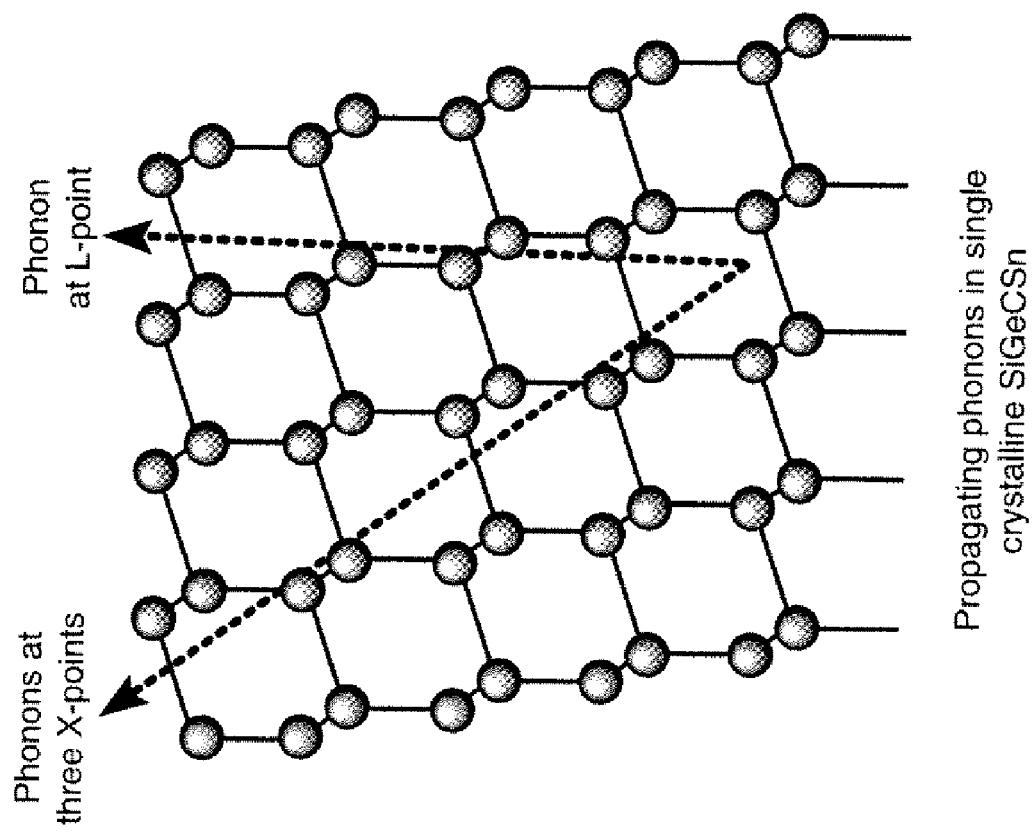

FIG. 10 shows scattering of phonons at the stacking faults between twin crystal 1001 and underlying original crystal 1002. The left panel (a) of FIG. 10 shows propagating phonons in single crystalline SiGeCSn. The right panel (b) shows a scattered phonon in highly-oriented twinned SiGeCSn. In order to conserve the momentum and energy of the traveling phonon in X-point of the original crystal, the phonon will be scattered as shown in FIG. 10.

The dotted phonon in L-point 1011 will travel in the same direction in the twin crystal because there is no change with stacking fault. The dotted phonon 1012 traveling in X-point [100] will be scattered at the stacking fault plane because it will face a new media, L-point [101] of twin crystal. We have to consider multiplicity of X-points. There are three X-points, [101], [110], and [011] around one L-point [111]. Therefore the stacking faults in (111) plane can scatter all phonons in three X-points. Similar scattering can occur to other orientations when there is difference in the phonon bands between original crystal and twin crystal.

Therefore, there is embedded phonon-scattering mechanism in highly-oriented twinned SiGeCSn alloy on the basal plane of trigonal substrate. In other words, the stacking fault in this novel material can create a phonon scattering effect without greatly reducing electrical conductivity. This phenomenon is analogous to another highly efficient thermoelectric material, Skutterudite CoSb, which has many poly-type structures to scatter phonons, yet they are electrically connected. The present invention provides Skutterudite-like SiGe alloy that is electrically well-connected, but scatters phonons with poly-type structure, i.e. twin crystal, made with stacking faults. Because a stacking fault is an atomic-size phenomenon, a high density of the stacking faults can be embedded into SiGeCSn material layer, and the sum of scattering effect can be very large, resulting in the large reduction of thermal conductance (K), as well as thermal diffusivity. This increases the ZT factor of thermoelectric SiGeCSn alloy on the basal plane of trigonal substrates, including (without limitation) SiGe, SiC and SiGeC on sapphire.

FIG. 11 shows the highly-oriented twinned SiGe thermoelectric materials (p-type and n-type) on c-plane sapphire wafers.

Thermoelectric Devices

Generally, the sapphire wafer is a very good thermal conductor with thermal conductivity of 42 W/mK at 20° C., 20 W/mK at 300° C., and 10 W/mK at 700° C. Thermoelectric devices should usually have low thermal conductivity to maintain the temperature difference between the hot side and cold side. In the case of SiGeCSn materials on sapphire in a plane device, sapphire could cause heat loss and reduce the temperature difference. One way to overcome this is to separate the SiGeCSn material from the sapphire in order to build a planar thermoelectric device with low thermal conductivity. However, there are some thermoelectric applications which do not need low thermal conductivity. One example is the electric power generation from automobile engine heat in which the engine temperature cannot be raised but has to be kept at constant temperature. Then, SiGeCSn on sapphire itself can be a good thermoelectric device.

Figures 12A, 12B:
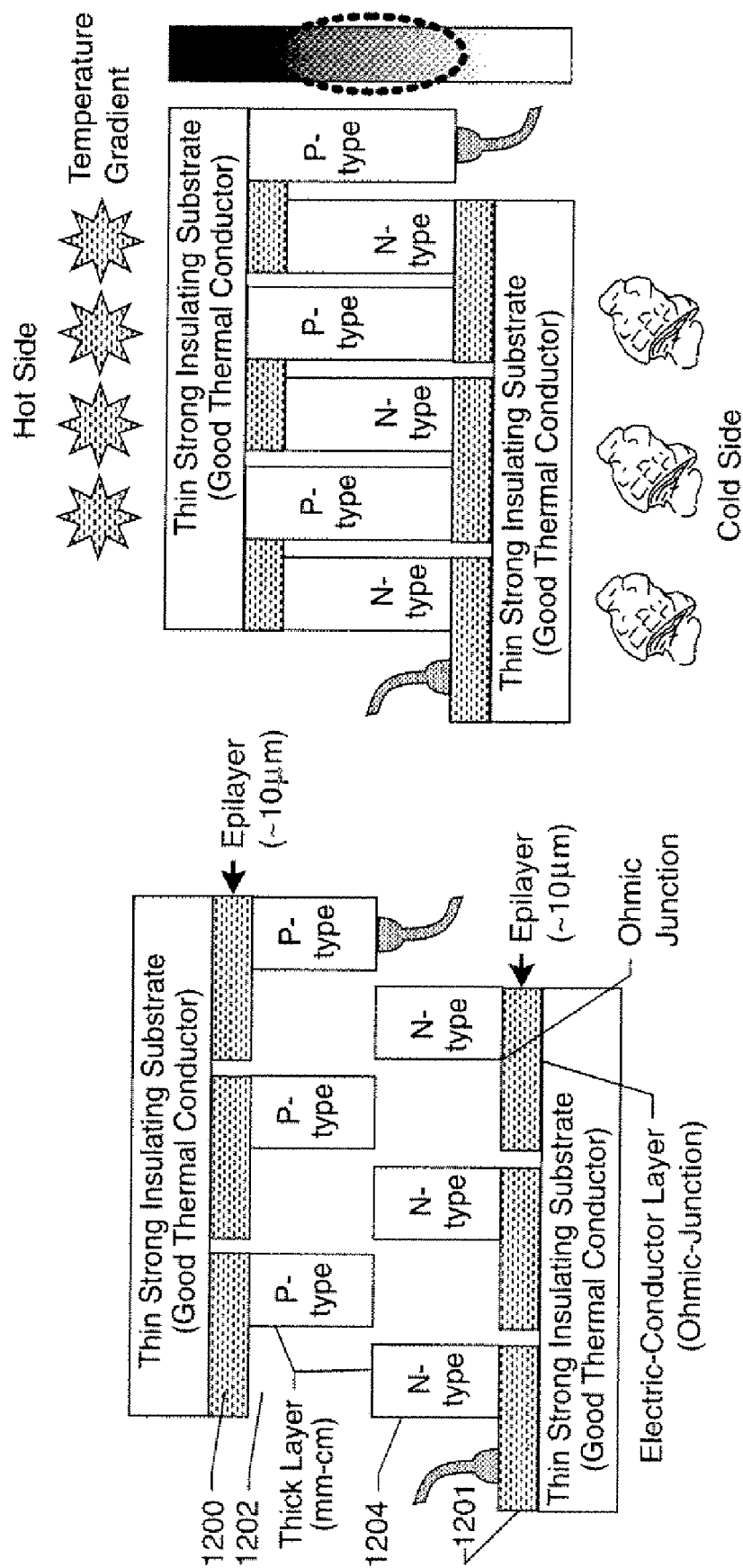
FIG. 12 shows (a) p-type and n-type SiGeCSn layer grown on two different basal plane trigonal wafers such as c-plane sapphire, with electrical circuit on the substrate made with n+ or p+ semiconductor layer, (b) assembled thermoelectric device made with two SiGeCSn/trigonal substrate wafers.

On the other hand, the highly-oriented twinned SiGeCSn alloy on sapphire can be used as it is, in the vertical temperature gradient configuration as shown in FIG. 12 and FIG. 13. High thermal conductivity of sapphire actually helps thermoelectric device performance in this configuration because most of the temperature gradient is applied on the thermoelectric material which has low thermal conductivity.

P-type and n-type of SiGeCSn alloys are grown on separate basal plane trigonal wafers with high thermal conductivity as shown in FIG. 12(*a*) (1202, 1204) and FIG. 13(*a*) (1302, 1304). The electric circuit on the wafer is made with heavily doped n+ and p+ semiconductor (1200, 1201) in FIG. 12(*a*). In FIG. 13(*a*), the electric circuit on the wafer is made with conducting materials such as metals (aluminum, tungsten, gold, etc.), semi-metals, silicides, germanicides, zinc oxide, indium tin oxide (ITO), and so on (1300, 1301). The thermoelectric materials can be made in columnar shapes with lithography, etching, and/or selective growth. The thickness of SiGeCSn thermoelectric materials can be any size between a few micro-meters and a few meters, but usually in a range from a few millimeters to a few centimeters.

Once the two wafers are fabricated with n-type SiGeCSn and p-type SiGeCSn respectively, two wafers will be bonded together to make a complete thermoelectric device as shown in FIG. 12(*b*) and FIG. 13(*b*). There are many available wafer-bonding and die-bonding methods such as anodic bonding. Any kind of bonding methods can be used as long as the interface is conductive. For the configuration of FIG. 13, the conducting materials with ohmic contact to thermoelectric materials have the best electrical properties.

Because the substrate has good thermal conductivity, most of the temperature change is located in the p-type and n-type thermoelectric materials because they have low thermal conductivity. Therefore, this structure maximizes the temperature difference across the thermoelectric materials and maximizes the electric power output.

Thus, it is apparent that the methods and materials described in the present disclosure satisfy the objects of the invention set forth above. Materials fabricated in accordance with the present invention can be advantageously employed in thermoelectric power generators, including radio-isotope thermoelectric generators, thermoelectric cooling devices, integrated TE cooling devices, thermal semiconductors, thermal sensors, and thermal barriers.

The present invention is further discussed in Y. Park, G. C. King, S. H. Choi, Rhombohedral epitaxy of cubic SiGe on trigonal c-plane sapphire, Journal of Crystal Growth 310 (2008) 2724-2731, herein incorporated by reference in its entirety.

Although the present invention has been described in detail, it should be understood that various changes, substitutions, and alterations may be readily ascertainable by those skilled in the art and may be made herein without departing from the spirit and scope of the present invention as defined by the following claims.

What is claimed as new and desired to be secured by Letters Patent of the United States is:

1. A thermoelectric cubic crystalline material comprising an alloy of two or more of silicon, germanium, carbon and tin, said cubic crystalline material having been fabricated on the basal plane of a trigonal or hexagonal crystalline substrate, said cubic crystalline material having been fabricated on said substrate such that the cubic crystals thereof (a) were highly oriented in the [111] direction relative to said basal plane of said substrate, and (b) contains greater than about 40% twin crystals.

2. The thermoelectric material of claim 1, wherein said cubic crystalline material further comprises a dopant.

3. The thermoelectric material of claim 2, wherein said dopant is a p-type dopant.

4. The thermoelectric material of claim 2, wherein said dopant is an n-type dopant.

5. The thermoelectric material of claim 3, wherein said p-type dopant is Boron.

6. The thermoelectric material of claim 4, wherein said n-type dopant is selected from the group comprising phosphorous and arsenic.

7. The thermoelectric material of claim 1, wherein said cubic crystalline material remains attached to said trigonal or hexagonal substrate.

8. The thermoelectric material of claim 1, wherein said cubic crystalline material has been separated from said trigonal or hexagonal substrate.

9. The thermoelectric material of claim 1, wherein said alloy of said cubic crystalline material is SiGe.

10. The thermoelectric material of claim 1, wherein said alloy of said cubic crystalline material is SiGeC.

11. The thermoelectric material of claim 1, wherein said alloy of said cubic crystalline material is SiC.

12. The thermoelectric material of claim 1, wherein said trigonal substrate is c-plane sapphire.

13. The thermoelectric material of claim 1, wherein said alloy comprises SiGe having an alloy composition of 0.40 Si and 0.60 Ge, said SiGe alloy is doped with Boron at a doping concentration of about $10^{18}$ atoms/cm$^3$, and said substrate is c-plane sapphire.

14. The thermoelectric material of claim 1, wherein said alloy is comprises SiGe having an alloy composition of 0.20 Si and 0.80 Ge, said SiGe alloy is doped with Boron at a doping concentration of about $10^{18}$ atoms/cm$^3$, and said substrate is c-plane sapphire.

15. The thermoelectric material of claim 1, wherein said alloy is comprises SiGe having an alloy composition of 0.1 Si and 0.9 Ge, said SiGe alloy is doped with Boron at a doping concentration of about $3 \times 10^{19}$ atoms/cm$^3$, and said substrate is c-plane sapphire.

16. A thermoelectric device made with a cubic crystalline material comprising an alloy of two or more of silicon, germanium, carbon and tin, said cubic crystalline material having been fabricated on the basal plane of a trigonal or hexagonal crystalline substrate, said cubic crystalline material having been fabricated on said substrate such that the cubic crystals thereof (a) were highly oriented in the [111] direction relative to said basal plane of said substrate, and (b) contains greater than about 40% twin crystals.

17. A thermoelectric device in accordance with claim 16 further comprising two vertically bonded wafers comprising said cubic crystalline material, one of said wafers being doped with n-type materials and the other of said wafers being doped with p-type materials.

18. A thermoelectric device in accordance with claim 17 further comprising one or more electrical circuit elements.

19. A thermoelectric device in accordance with claim 18 wherein said one or more electrical circuit elements make a serial connection between said n- and p-type thermoelectric materials.

20. A thermoelectric device in accordance with claim 18 wherein said one or more electrical circuit elements make a parallel connection between said n- and p-type thermoelectric materials.

21. A thermoelectric device in accordance with claim 18 wherein said one or more electrical circuit elements comprises a heavily doped p- or n-type semiconductor.

22. A thermoelectric device in accordance with claim 18 wherein said one or more electrical circuit elements comprises conducting materials selected from the group consisting essentially of metals, semi-metals, silicides, germanicides, zinc oxide, and indium tin oxide (ITO).

23. A thermoelectric device in accordance with claim 18 wherein said one or more electrical circuit elements comprises conducting materials selected from the group consisting essentially of metals, semi-metals, silicides, germanicides, zinc oxide, and indium tin oxide (ITO).

24. A thermoelectric device in accordance with claim 23 said conducting material is a metal selected from the group consisting essentially of aluminum, tungsten, and gold.

* * * * *